(12) United States Patent
Clark

(10) Patent No.: US 7,175,502 B2
(45) Date of Patent: Feb. 13, 2007

(54) AREOLA PAD

(76) Inventor: Kathrine Clark, 10837 Scaggsville Rd., Laurel, MD (US) 20723

( * ) Notice: Subject to any disclaimer, the term of this patent is extended or adjusted under 35 U.S.C. 154(b) by 0 days.

(21) Appl. No.: 11/241,916

(22) Filed: Oct. 4, 2005

(65) Prior Publication Data

US 2006/0030239 A1    Feb. 9, 2006

Related U.S. Application Data

(62) Division of application No. 10/830,318, filed on Apr. 23, 2004, now Pat. No. 6,962,519.

(51) Int. Cl.
*A41C 3/06* (2006.01)
*A41C 3/12* (2006.01)

(52) U.S. Cl. .......................... 450/37; 450/57; 128/889; 604/385.07; 2/267

(58) Field of Classification Search ................ 450/37, 450/39, 54–57; 128/889, 890; 604/385.07; 2/267
See application file for complete search history.

(56) References Cited

U.S. PATENT DOCUMENTS

| | | |
|---|---|---|
| 3,749,102 A | 7/1973 | Wynants |
| 4,270,538 A | 6/1981 | Murphy |
| 4,333,471 A | 6/1982 | Nakai |
| 4,754,750 A | 7/1988 | Imonti |
| 4,870,977 A | 10/1989 | Imonti |
| 5,004,473 A | 4/1991 | Kalantar |
| 5,032,103 A | 7/1991 | Larsson |
| 5,394,889 A * | 3/1995 | Morrissey et al. .......... 128/845 |
| 5,522,892 A | 6/1996 | Lin |
| 5,531,231 A * | 7/1996 | Morrissey et al. .......... 128/846 |
| 5,782,672 A | 7/1998 | Woodley |
| 5,998,693 A | 12/1999 | Zagame |
| 6,039,629 A | 3/2000 | Mitchell |
| 6,063,110 A | 5/2000 | Stedman |
| 6,074,272 A | 6/2000 | Hebert |
| 6,241,715 B1 | 6/2001 | Houser et al. |

OTHER PUBLICATIONS

Nipple Shield Brochure, Medela. (undated).
Contact Nipple Shield, Medela, 2 pages. (undated).
Hobbit Brochure, Medela. (undated) internet advertisement (Jun. 25, 2002).
Medela Contact Nipple Shield, 2 pages. internet advertisement (Jun. 25, 2002).
Nipple Shields by Tamar Krantman Weiss, 2 pages. internet advertisement (undated).
Breast Care, 1 page. internet advertisement (undated).

* cited by examiner

*Primary Examiner*—Gloria Hale
(74) *Attorney, Agent, or Firm*—Wenderoth, Lind & Ponack, L.L.P.

(57) ABSTRACT

The invention provides an areola pad for use during breast feeding. The invention is used to treat sore and painful nipples caused by breast feeding and to enable uninterrupted nursing. The invention includes a flexible element composed of one or more bio-compatible polymers, where the element is breathable, and allows contact between the mother and the infant. The flexible element further includes a centrally-located opening for receiving a nipple of any size, where the nipple extends through the opening and is uncovered.

23 Claims, 2 Drawing Sheets

AREOLA PAD

This application is a divisional of Ser. No. 10/830,318 filed Apr. 23, 2004, now issued as U.S. Pat. No. 6,962,519.

FIELD OF THE INVENTION

This invention relates to an areola pad useful for treating sore or painful nipples, for example in women who are breast feeding. The areola pad includes a flexible element having a centrally located opening through which the nipple extends. The areola pad can be worn during breast feeding.

BACKGROUND OF THE INVENTION

It is well known that breast feeding is highly recommended and preferred over bottle feeding. The physical experience of breast feeding enhances bonding between the mother and baby. Further, breast milk provides immunoglobulins to the baby, thus conferring passive immunity to the baby through the mother.

However, virtually every mother who attempts to breast feed her baby experiences sore and painful nipples at some point. For many women, this can lead to cracked, bleeding nipples, and even breast infections. Such experiences cause many women to abandon breast feeding. Presently, there is no satisfactory treatment for these conditions that provide immediate relief. Typically, doctors prescribe topical preparations including, for example, lanolin, to ease soreness, and recommend air drying nipples. However, it is generally difficult to breast feed while using such preparations as an infant nurses every two to three hours and topical solutions need to be removed. Also, it is very difficult in today's world to "air dry" nipples.

Devices including nipple shields are known and include the Medela™ Contact Nipple Shield made by Medela, Inc., of McHenry, Ill. This shield is worn over the nipple and areola, and is designed to help correct latch-on difficulties, especially in the case of women who have inverted nipples. The shield has holes in the nipple area to allow breast milk to flow through. The shield also includes a cut-away portion in the base area (in the area of the areola). The Medela™ shield is available in different sizes to accommodate different sized nipples.

Doctors do not recommend using nipple shields like the Medela™ shield to treat sore nipples, because such use does not correct the underlying problem (incorrect latching-on) and creates additional problems. Specifically, use of such shields causes the mother to receive less stimulation, thus causing a decrease in milk production, and thereby causing diminished milk supply and diminished weight gain of the baby. Other problems associated with the use of such shields include: nipple confusion, whereby the baby may become so used to the shield that he or she may refuse the mothers natural nipple; a decreased ability of the baby to smell and feel the mother; and a negative effect on bonding between the baby and the mother.

Another available nipple shield is the Hobbit™ Breast Shell, made by Medela, Inc. of McHenry, Ill. The Hobbit™ Breast Shells are for protecting sore nipples from further irritation. The Hobbit™ Breast Shell is a rigid, dome-shaped, multi-piece shell which overlies the areola and nipple to protect them from irritation, for example from clothing. The shell includes through holes which allow air to circulate around the nipple. The Hobbit™ Breast Shell cannot be worn during breast feeding.

Neither of these devices, nor known treatments, help to ease pain and soreness during breast feeding. Thus, there is a great need for a device which eases pain and soreness during breast feeding, where nipple stimulation is unaffected by the device, which preserves the baby's ability to smell and feel the mother, that does not give rise to nipple confusion, and accommodates nipples and areola of all sizes.

SUMMARY OF THE INVENTION

The invention provides an areola pad including a flexible element, including a centrally located opening through which a nipple extends, where the majority of the nipple is not covered.

The invention provides an areola pad where the flexible element is substantially flat.

The invention further provides an areola pad where the areola pad is substantially round.

The invention also provides an areola pad where the substantially round areola pad includes a bottom annular edge.

The invention provides an areola pad where the bottom annular edge defines a flange.

The invention provides an areola pad where the pad substantially covers the areola.

The invention provides an areola pad where the pad covers at least sixty percent of the areola.

The invention provides an areola pad where the pad covers at least seventy percent of the areola.

The invention provides an areola pad where the pad covers at least eighty percent of the areola.

The invention also provides an areola pad including a flexible, substantially dome-shaped element including an outer convex surface; an opposing inner concave surface to receive an areola and nipple; and a centrally located opening through which said nipple extends, where the nipple is not covered.

The invention further provides an areola pad where the flexible, substantially dome-shaped element is a breathable element.

The invention also provides an areola pad where the flexible element is substantially flat.

The invention provides an areola pad, where the flexible, substantially flat element is a breathable element.

The invention provides an areola pad where the breathable element includes one or more openings.

The invention further provides an areola pad where the openings include one or more through-holes.

The invention provides an areola pad, where the openings include one or more slits.

The invention provides an areola pad, where the one or more slits are provided on a substantially flat flexible element and configured such that said areola pad conforms to the shape of an areola, when placed on said areola.

The invention also provides an areola pad, including one or more bio-compatible polymers.

The invention provides an areola pad, where the one or more bio-compatible polymers include one or more silicone based polymers.

The invention further provides an areola pad, where the one or more bio-compatible polymers include a bio-compatible porous membrane.

The invention provides an areola pad, where the centrally located opening includes one or more centrally located, opposing, overlapping slits traversing said flexible element.

The invention further provides an areola pad, where the centrally located opening includes a through-hole having an annular edge.

The invention also provides an areola pad, where the through-hole further includes one or more slits traversing the flexible element, and intersecting the annular edge.

The invention provides an areola pad, where the flexible element has a thickness in the range of from about 0.5 mm to about 5.0 mm.

The invention provides an areola pad that does not include an adhesive.

The invention also provides an areola pad, where the through-holes include one or more shapes selected from the group of circular, oval, square, triangular, rectangular, and irregular.

The invention further provides an areola pad, where the areola pad is sterile and disposable.

The invention also provides a multi-use areola pad.

The invention provides an areola pad, where the biocompatible polymer includes a cast mesh.

The invention provides an areola pad, where the biocompatible polymer includes a woven mesh.

The invention also provides an areola pad which is prelubricated on the inside surface with a thin film of lanolin.

DETAILED DESCRIPTION OF THE PREFERRED EMBODIMENT(S)

Figure 1:
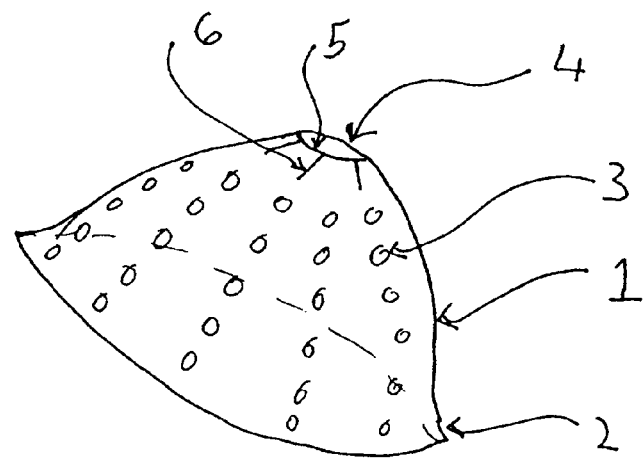
FIG. 1 is a perspective view of the dome-shaped areola pad having a plurality of through-holes; a centrally located opening defined by a through-hole and slits traversing the flexible element, and intersecting the annular edge of the through-hole; and a bottom annular edge defining a flange.

A. Definitions:

The below definitions serve to provide a clear and consistent understanding of the specification and claims, including the scope to be given such terms.

Breast:
By the term "breast" is intended for the purposes of the invention, a female, human breast including the nipple and the areola.

Nipple:
By the term "nipple" is intended for the purposes of the invention, a projection at the apex of the breast on the surface of which the lactiferous ducts open.

Areola:
By the term "areola" is intended for the purposes of the invention, the circular, pigmented area surrounding the nipple.

Biocompatible Polymer:
By the term "biocompatible polymer" is intended for the purposes of the invention, one or more polymeric materials which when in contact with the human body does not provoke an adverse response in the patient. A suitable bio-compatible polymer when in contact with the human body is not toxic nor injurious to the person, and does not cause an immunological response, and include for example, silicone and silicone-based polymers; polytetrafluoroethylene (ePTFE); a natural hydrogel; a synthetic hydrogel; TEFLON (polytetrafluoroethylene); silicone, polyurethane; polysulfone; cellulose; polyethylene; polypropylene; polyamide; polyester; and a combination of two or more of these materials. Examples of natural hydrogels include fibrin, collagen, elastin, and the like. polyethylene terephthalate (PET), polyurethane urea and silicone.

Dome-Shaped:
By the term "dome-shaped" is intended for the purposes of the invention, any shape whereby an interior area is defined sufficient to conform to the areola of the human breast. Suitable shapes include very slightly curved, slightly curved, curved, and conical.

Opening:
By the term "opening" is intended for the purposes of the invention, any void space or lack of continuity in the flexible element, including but not limited to pores, through-holes, and slits.

Through-Hole:
By the term "through-hole" is intended for the purposes of the invention, an opening traversing the thickness of the flexible element of the areola pad, where the opening can be of any shape. Suitable shapes include any geometric or curved shape, including but not limited to: circular, oval, square, rectangular, triangular, and irregular.

Porous Membrane or Film:
By the term "porous membrane or film" is intended for the purposes of the invention, any breathable membrane or film composed of an accepted biocompatible polymer having openings that pass directly or indirectly through the polymer.

Breathable:
By the term "breathable" is intended for the purposes of the invention, a biocompatible polymeric material that allows air to pass through, i.e. air permeable. Such breathability can be achieved using a porous bio-compatible polymer membrane or film; or by providing a bio-compatible material with openings including for example, slits, pores or through-holes; for example by providing a membrane, sheet, or film with such openings, by for example heat-forming or cutting, or by casting a bio-compatible polymer using a cast to create slits, pores or through-holes.

B. Making and Using the Inventive Areola Pad

The areola pad is composed of any flexible, bio-compatible polymer. Other suitable biocompatible polymers include those flexible bio-compatible polymers that become more pliant and flexible when exposed to heat, for example when used in contact with the human body. Such polymers include silicone-based bio-compatible polymers, including for example, silicone.

The areola pad is preferably breathable, with breathability being achieved by any method including use of a flexible, bio-compatible, porous membrane or film. Alternatively, a bio-compatible polymeric material can be provided with openings sufficient to allow air to pass through. Suitable openings can be achieved by providing the bio-compatible polymeric material with slits, through-holes, or pores. Such openings can be of any size, configuration, or shape, such that the resultant areola pad is breathable. In addition, the openings can be configured based upon the amount of skin to skin contact desired between the baby and the mother. Such openings can be provided in a sheet of biocompatible polymeric membrane or film, or can be created by forming the areola pad with such openings, for example when the polymeric material is cast. When a substantially flat areola pad is desired, it is preferable to provide slits in the flexible element configured such that the areola pad conforms to the shape of an areola, when placed on the areola.

The areola pad can be of any shape but is preferably substantially circular, and is either substantially flat or dome-shaped. The substantially flat pad can be made by simply cutting the flexible element from a sheet of flexible, bio-compatible polymeric material, or by casting the bio-compatible polymeric material. The dome-shaped flexible element can be made by forming, for example using heat, a sheet of flexible, bio-compatible polymeric material, or by casting.

The dome-shaped element may optionally include a flange at its bottom edge. Such methods of cutting, forming, and casting, are well-know to those of ordinary skill in the art to which the invention applies, and can be readily employed without undue experimentation.

The pores, slits and/or through-holes, provided in the flexible element to confer breathability, and contact between the baby and the mother, can be of any size and any shape, provided air can pass through the flexible element. Suitable average diameters for through-holes are from about 0.5 mm to about 10.0 mm, from about 2.0 mm to about 8.0 mm, and from about 3.0 mm to about 5.0 mm. Suitable slit lengths are from about 3.0 mm to about 3.0 cm, from about 5.0 mm to about 2.0 cm, and from about 7.0 mm to about 1.5 cm.

The centrally-located opening is provided to fit around the base of the nipple, leaving the rest of the nipple free and uncovered. The opening can be a through-hole, a through-hole provided with one or more slits around its perimeter, or opposing, overlapping slits. The slits either in conjunction with the through-hole, or alone (opposing and overlapping) enable the areola pad to closely fit any size nipple.

When the opening is opposing, overlapping slits, the slit length is from about 7.0 mm to about 2.5 cm, and from about 1.0 cm to about 2.0 cm. The flaps created by such slits can be shaped as desired, for example, the flaps can be rounded to remove any pointed edges.

Where the opening is a centrally-located through-hole provided with one or more slits to confer a comfortable fit, the slit length is from about 3.0 mm to about 1.5 cm, and from about 5.0 mm to about 1.0 mm, depending on the diameter of the centrally-located through-hole. For example, when the centrally-located through-hole is small, that is from about 2.0 mm to about 5.0 mm, the slit length is longer, and when the through-hole is larger, for example greater than 5.0 mm, the slit length is shorter.

The areola pad has a diameter of from about 3.0 cm to about 9.0 cm, from about 4.0 cm to about 8.0 cm, or from about 5.0 cm to about 7.0 cm.

The areola pad may have a raised lip or tab at its edge to help the mother remove or readjust the pad whilst the baby nurses. The tab may be U-shaped and have a size of about ¾ inch long and ½ inch wide.

The areola pad is provided in a sterile, single-use, disposable form, and in a prelubricated (lanolin) form. To use the areola pad, the pad is removed from the sterile packaging in the case of the single use pads, and placed over the nipple and contacting the areola, such that the nipple extends through the centrally-located opening of the pad. Once the pad is in place, the mother can breast feed.

The areola pad provides a buffer between the areola and the infants mouth which helps to reduce pain caused by sore nipples, and promotes healing. Further the areola pad allows skin contact between the mother and the baby, thus enabling the baby to smell the mother. Such contact is necessary and very important in the bonding process. Further, since the nipple is uncovered, the mother receives adequate stimulus which ensures adequate production of milk. The inside surface of the areola pad may be lubricated with a thin film of lanolin to aid in protection and/or healing of the nipple. The areola pad stays in place with contact from the baby including when the device has the addition of the lanolin lubrication layer.

C. Pore Formation

In one method according to the invention, a porous polyurethane sheet material (i.e., film) can be made by dissolving a polyether urethane in an organic solvent such as 1-methyl-2-pyrrolidone; mixing into the resulting polyurethane solution a crystalline, particulate material like a salt or sugar that is not soluble in the solvent; casting the solution with particulate material into a thin film; and then applying a second solvent, such as water, to dissolve and remove the particulate material, thereby leaving a porous sheet. Such a method is disclosed, for example, in U.S. Pat. Nos. 5,599,352 and 5,591,227, both issued to Dinh et al. A portion of the particulate material may remain within the film. As a result, it is preferred that the solid particulate material be bio-compatible.

In yet another method, a solvent in which the polymer (i.e., a film-forming polymer) is soluble that is capable of phase separating from the polymer at a reduced temperature can be used to prepare a porous polymer film. In this method a solution of the desired polymer, such as polyurethane, dissolved in a solvent, such as dioxane, is added to the mold. The temperature of the solution is then reduced to a temperature at which the solvent freezes and phase separates from the polymer as it forms a film, thereby forming particulate material (i.e., frozen solvent particles) in situ. Typically, for polyurethane in dioxane, this is a temperature of about −70.degree. C. to about 3. degree. C. The composition is then immersed in an ice cold water bath (at about 3. degree. C.) for a few days to allow the dioxane to dissolve into the ice cold water, thereby forming pores. The number and size of the pores can be controlled by the concentration of the polymer and the freezing temperature. A method similar to this is disclosed in Liu et al., J. Biomed. Mater. Res., 26, 1489 (1992). This method can be improved on by using a two-step freezing process described herein. In a first step, the mixture is cooled slowly to create a first fraction of particulate material (i.e., frozen solvent particles) dispersed within solidified polymer. In a second step, the mixture is cooled further (and more quickly) to create a second fraction of particulate material of smaller size dispersed within solidified polymer. In this way, a wider range of pore sizes can be formed with greater control. This modified method is further described in Example 6.

With regard to woven mesh bio-compatible material, suitable materials include fibers including PTFE, collagen, and natural wool proteins. PTFE is an expansible, bio-compatible material which has an extensive history of use in the medical field. Similarly, collagen, which is available in a number of forms from Collagen Corp. of Palo Alto, Calif., is a bio-compatible material which has been used in medical applications.

D. Suitable Polymer Materials

Suitable polymers include: silicone, silicone based polymers, ether derivatives of a polysaccharide including semi-synthetic polymers, and includes acid ether derivatives of polysaccharides including for example, cellulosics including for example, methyl cellulose, carboxy methyl cellulose, hydroxy propyl cellulose, and hydroxy ethyl cellulose; semi-synthetic polymers including any polymer which is water soluble of the semi-synthetic type, and being a macromolecule formed by the chemical union of five or more identical combining units called monomers, and includes chemically treated natural polymers including but not limited to: cellulosics including for example rayon, methyl cellulose, carboxy methyl cellulose, hydroxy propyl cellulose, hydroxy ethyl cellulose, cellulose acetate, and other cellulose ethers; and modified starches including for example acetates and ethers including for example, starch acetate. Water-soluble ethers are preferred semi-synthetic polymers, less water-soluble semi-synthetic polymers may also be used, for example with a biocompatible solvent that is miscible in water and include cellulose plastics including for example cellulose acetate phthalate.

E. The Figures

FIG. 1 illustrates an areola pad having a dome-shaped, flexible element 1, where the flexible element 1 is a bio-compatible polymer, for example, silicone. The flexible element 1 has a bottom annular edge defining a flange 2. The flexible element 1 is provided with a plurality of through-holes 3. A centrally-located opening 4 is provided in the flexible element 1, and includes a centrally located through-hole 5 and slits 6 provided around the through-hole to confer fit.

Figure 2:
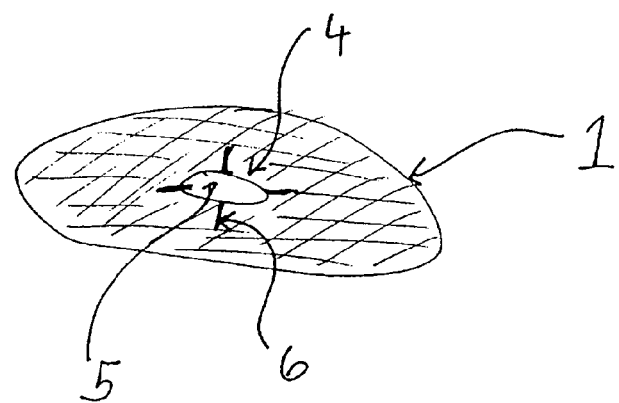
FIG. 2 is a perspective view of the substantially flat areola pad including a woven mesh; and a centrally located opening defined by a through-hole and slits traversing the flexible element, and intersecting the annular edge of the through-hole.

FIG. 2 illustrates a substantially flat areola pad having a flat, bio-compatible, polymeric woven mesh, flexible element 1, and a centrally-located opening 4 which includes a centrally located through-hole 5 and slits 6 provided around the through-hole to confer fit.

Figure 3:
FIG. 3 is a cross-section of the dome-shaped areola pad having a plurality of through-holes.

FIG. 3 illustrates a cross-section of an areola pad having a dome-shaped, flexible element 1, a plurality of through-holes 3, a centrally-located opening which is a through-hole 5, and a flange 2.

Figure 4:
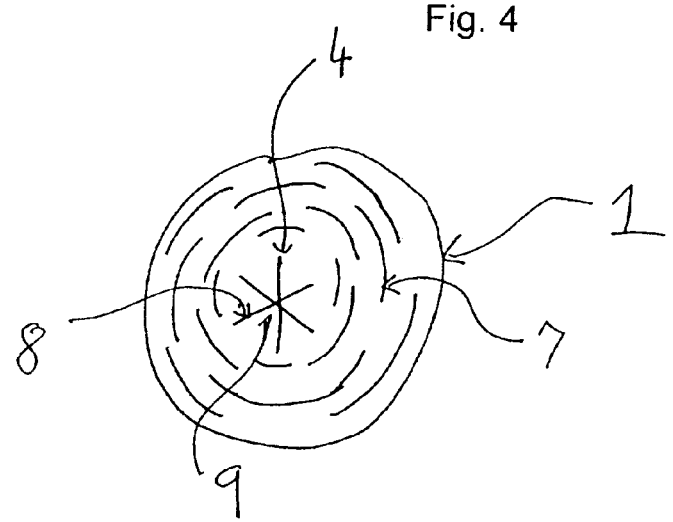
FIG. 4 is a top-down view of the substantially flat areola pad having a centrally located opening defined by opposing, overlapping slits; and including a plurality of slit openings configured such that the areola pad conforms to the shape of an areola, when placed on the areola.

FIG. 4 illustrates a top-down view of an areola pad having a substantially flat, flexible element 1, provided with a plurality of slits 7 configured to conform to the shape of the areola when in use. The flexible element 1 has a centrally-located opening 4 including opposing, overlapping slits 8. The slits 8 serve to confer fit, and define flaps 9. Flaps 9 can be shaped as desired, for example, to round any pointed edges.

Figure 5:
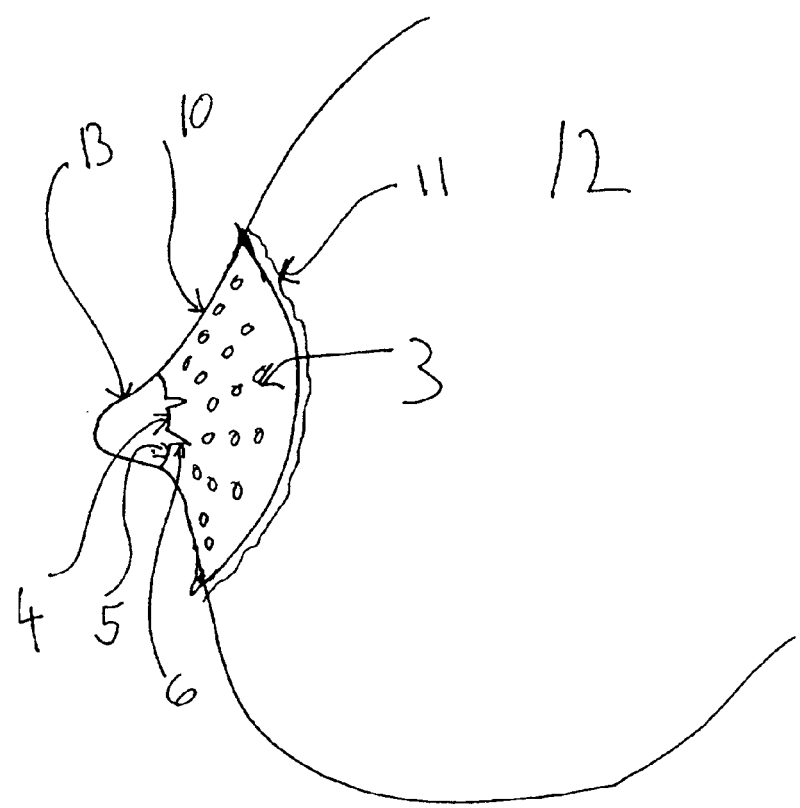
FIG. 5 is a perspective view of the dome-shaped areola pad having a centrally located through-hole and slits traversing the flexible element, and intersecting the annular edge of the through-hole; an annular flange; and a plurality of through-holes, in contact with the areola of the breast.

FIG. 5 illustrates the areola pad 10 in use and placed in contact with the areola 11 of a woman's breast 12, such that the nipple 13, extends through the centrally-located opening 4 of the flexible element 1. The centrally-located opening 4 includes a centrally located through-hole 5 and slits 6 provided around the through-hole 4 to confer fit. The flexible element 1 is provided with through-holes 3.

All references cited are hereby incorporated by reference. Now having fully described this invention, it will be understood by those of skill in the art that the scope may be performed within a wide and equivalent range of conditions, parameters, and the like, without affecting the spirit or scope of the invention or of any embodiment thereof.

I claim:

1. An areola pad for placement on the areola, consisting of:
a single pliant flexible sheet of a sterile breathable bio-compatible polymer membrane which is substantially circular in shape and adapted to substantially only cover a wearer's areola, said pad having a centrally located opening through which a wearer's nipple extends when said areola pad is placed on said wearer's areola, and said pad having a plurality of through-holes.

2. The areola pad of claim 1, wherein the flexible sheet is a flexible, substantially dome-shaped element, comprising: an outer convex surface; an opposing inner concave surface to receive an areola and nipple; and a centrally located opening through which said nipple extends, wherein said nipple is not covered.

3. The areola pad of claim 1, wherein said flexible sheet is substantially flat.

4. The areola pad of claim 1, wherein the biocompatible polymer membrane comprises one or more bio-compatible polymers.

5. The areola pad of claim 4, wherein said one or more bio-compatible polymers comprise one or more silicone based polymers.

6. The areola pad of claim 4, wherein said one or more bio-compatible polymers form a porous membrane.

7. The areola pad of claim 2, wherein said centrally located opening comprise one or more centrally located, opposing, overlapping slits traversing said flexible element.

8. The areola pad of claim 2, wherein said centrally located opening comprise a through-hole having an annular edge.

9. The areola pad of claim 8, wherein said through-hole further comprise one or more slits traversing said flexible sheet, and intersecting said annular edge.

10. The areola pad of claim 2, wherein said flexible sheet has a thickness in the range of from about 0.5 mm to about 5.0 mm.

11. The areola pad of claim 2, wherein said areola pad does not comprise an adhesive.

12. The areola pad of claim 1, wherein said through-holes comprise one or more shapes selected from the group consisting of: round, oval, square, triangular, rectangular, and irregular.

13. The areola pad of claim 2, wherein said areola pad is disposable.

14. The areola pad of claim 13, wherein said areola pad is a multi-use areola pad.

15. The areola pad of claim 1, wherein said areola pad covers at least sixty percent of said areola.

16. The areola pad of claim 15, wherein said areola pad covers at least seventy percent of said areola.

17. The areola pad of claim 16, wherein said areola pad covers at least eighty percent of said areola.

18. The areola pad of claim 4, wherein said bio-compatible polymer membrane comprises a cast mesh.

19. The areola pad of claim 4, wherein said bio-compatible polymer membrane comprises a woven mesh.

20. The areola pad of claim 2, wherein said areola pad comprises a bottom annular edge.

21. The areola pad of claim 20, wherein said bottom annular edge defines a flange.

22. The areola pad of claim 2, which is lubricated on its inside surface with a thin film of lanolin.

23. A method for treating sore nipples, comprising: placing the areola pad of claim 1, in contact with an areola of a patient, wherein the patient's nipple extends through the pad and remains uncovered.

* * * * *